(12) United States Patent
Matsumori et al.

(10) Patent No.: US 9,572,532 B2
(45) Date of Patent: Feb. 21, 2017

(54) BUTTON SENSOR

(75) Inventors: Barry Alan Matsumori, San Diego, CA (US); Kenneth Kaskoun, San Diego, CA (US); Matthew Nowak, San Diego, CA (US); Nicholas Yu, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 1353 days.

(21) Appl. No.: 12/358,602

(22) Filed: Jan. 23, 2009

(65) Prior Publication Data

US 2010/0191072 A1 Jul. 29, 2010

(51) Int. Cl.
*A61B 5/00* (2006.01)
*G06F 19/00* (2011.01)
*A61B 5/02* (2006.01)
*G08B 21/04* (2006.01)
*G06F 1/16* (2006.01)

(52) U.S. Cl.
CPC ........ *A61B 5/6804* (2013.01); *A61B 5/0024* (2013.01); *A61B 5/02* (2013.01); *A61B 5/6802* (2013.01); *G06F 1/163* (2013.01); *G06F 19/3418* (2013.01); *G08B 21/0438* (2013.01); *A41D 2300/32* (2013.01); *A61B 5/002* (2013.01); *A61B 5/0006* (2013.01); *A61B 5/0008* (2013.01); *Y10T 29/49002* (2015.01)

(58) Field of Classification Search
CPC ....... A61B 5/02; A61B 5/0024; A61B 5/6804; A61B 5/6802; G06F 19/3418; G06F 1/163; A41D 2300/32–2300/332; G08B 21/0438–21/0461; B29C 39/003

USPC ........ 600/300, 301, 372–391; 128/903–905, 128/920

See application file for complete search history.

(56) References Cited

U.S. PATENT DOCUMENTS

| | | | |
|---|---|---|---|
| 5,912,653 A | 6/1999 | Fitch | |
| 5,923,253 A * | 7/1999 | Anastasiou | 340/573.1 |
| 5,958,466 A * | 9/1999 | Ong | 425/127 |
| 6,279,170 B1 | 8/2001 | Chu | |
| 2006/0202816 A1* | 9/2006 | Crump | A61B 5/02055 340/539.12 |
| 2006/0250259 A1 | 11/2006 | Izumi | |
| 2007/0179372 A1* | 8/2007 | Say et al. | 600/347 |

(Continued)

FOREIGN PATENT DOCUMENTS

| | | |
|---|---|---|
| DE | 102007027899 | 12/2008 |
| EP | 1800599 | 6/2007 |

(Continued)

OTHER PUBLICATIONS

International Search Report and Written Opinion—PCT/US2010/021841, International Search Authority—European Patent Office—Jun. 4, 2010.

(Continued)

*Primary Examiner* — William Thomson
*Assistant Examiner* — Marie Archer
(74) *Attorney, Agent, or Firm* — Brian Momeyer

(57) ABSTRACT

A hermetically sealed electronic closure device, or button, includes a self-renewing power source, a sensor for measuring a metric, a memory storing information, a data processing circuit for controlling operations of the device, and a transceiver for sending and receiving information. The device is a standard part of a clothing item that is inconspicuous to a wearer of the clothing item.

20 Claims, 5 Drawing Sheets

(56) References Cited

U.S. PATENT DOCUMENTS

| | | | |
|---|---|---|---|
| 2007/0219597 A1* | 9/2007 | Kamen et al. | 607/60 |
| 2008/0001735 A1* | 1/2008 | Tran | 340/539.22 |
| 2008/0094775 A1* | 4/2008 | Sneh et al. | 361/275.3 |
| 2008/0139894 A1* | 6/2008 | Szydlo-Moore et al. | 600/300 |
| 2008/0146890 A1* | 6/2008 | LeBoeuf | A61B 5/0059 600/300 |
| 2008/0246439 A1* | 10/2008 | Tsui | H02J 7/0055 320/137 |
| 2008/0255794 A1* | 10/2008 | Levine | 702/141 |
| 2008/0287769 A1* | 11/2008 | Kurzweil et al. | 600/388 |
| 2009/0045966 A1* | 2/2009 | Rocznik | 340/573.7 |
| 2009/0054737 A1* | 2/2009 | Magar et al. | 600/300 |
| 2009/0084432 A1* | 4/2009 | Kosmehl | 136/251 |
| 2009/0111393 A1* | 4/2009 | Scalisi et al. | 455/90.1 |
| 2010/0185076 A1* | 7/2010 | Jeong et al. | 600/388 |

FOREIGN PATENT DOCUMENTS

| | | |
|---|---|---|
| EP | 1800599 A1 | 6/2007 |
| FI | 115424 | 4/2005 |
| GB | 2396043 | 6/2004 |

OTHER PUBLICATIONS

Hannikainen et al., "Button Component Encasing for Wearable Technology Applications," iswc,pp. 204-205, Ninth IEEE International Symposium on Wearable Computers (ISWC'05), 2005.
International Search Report—PCT/US2010/021841, International Search Authority—European Patent Office—Jun. 4, 2010.
Written Opinion—PCT/US2010/021841, International Search Authority—European Patent Office Jun. 4, 2010.

\* cited by examiner

BUTTON SENSOR

TECHNICAL FIELD

This application relates in general to sensors, and more specifically to a button biosensor located on an article of clothing.

BACKGROUND

Currently, biosensors are used to measure various characteristics of a living being. For example, some sensors measure heart rate or temperature. The sensors wirelessly relay data to a data recording device to monitor the health of the being. The sensor is typically attached to the being by an adhesive bandage. Because the sensor bandage is not physically connected to the data recording device, the sensor uses a battery for power.

SUMMARY

The present disclosure is directed to systems and methods that involve a device for collecting data of a metric, the device being located on a garment.

In one embodiment, a button sensor is adapted for use on a garment. The sensor is adapted to provide data of a metric related to a wearer of the garment, and includes a transmitter adapted to transmit the data; and a power source adapted to provide power to the transmitter. The button sensor is adapted to be secured to a portion of the garment.

In another aspect, a method manufactures a button. The method includes constructing a button sensor comprising a sensor adapted to measure data of a metric related to a wearer of a garment, a transmitter adapted to transmit the data to a receiver, and a power source adapted to provide power to the transmitter. The method also includes hermetically sealing the button sensor inside the button.

In still another aspect, a method of collecting data by use of a garment including a button sensor is presented. The method includes placing the garment on a wearer; and using the button sensor to measure data of a metric related to the wearer of the garment. The method also includes receiving the data from the button sensor.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION

Figure 1:
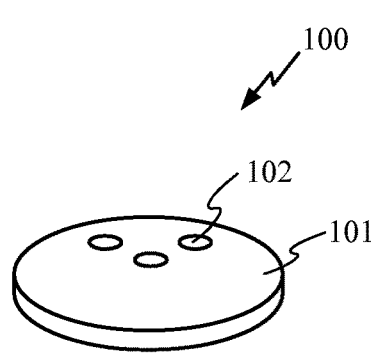
FIG. 1 depicts a perspective view of a button sensor.

The current arrangements for attaching biosensors to a living being have several shortcomings associated with them. One issue is that the sensor bandages are uncomfortable for the user. The adhesive material used to secure the sensor bandage to the body can be irritating to the skin. Another issue is that the sensor bandage may fall off of the body. The adhesive material tends to breakdown quickly from exposure to sweat and moisture. The adhesive material also loses effectiveness as the skin exfoliates skin cells. Thus, the bandage typically needs to be changed after a few days. A further issue is that the bandages cannot be cleaned, and after a short period of time may become dirty. Again, the bandage typically needs to be changed after a few days. A still further issue is that the bandage sensor requires the conscious effort to attach the sensor to the body of the user. The living being may be a human, a domesticated animal (e.g. a dog, cat, horse, cow, etc.), or an undomesticated animal (e.g. a tiger, elephant, cougar, etc.).

Embodiments of the invention provide a button that comprises a self-contained biosensor, where the button is located on an article of clothing. The sensor button solves the issues described above. The button sensor is not uncomfortable to wear and does not use an adhesive to attach itself to the body. The button sensor is hermetically sealed, and thus is not affected by moisture or sweat. Also, because it is hermetically sealed, the button sensor may be washed along with the garment to which it is attached. The button sensor does not require separate conscious effort by the user. The user would merely put on the garment or article of clothing, e.g., a shirt or pants, and then the button is operative.

A garment may have one or more buttons according to embodiments of the invention. Examples of a garment include a shirt, a pair of pants, a hat, a mask, underwear, a brassier, a hospital gown, a vest, a belt, jewelry (such as a bracelet, a necklace, a wristwatch, a ring), glasses, a hand bag, a wallet, a jacket, a sweat band, socks, shoes, and boots.

The button sensor may serve a function for the garment to which it is attached. For example, the button may be used to hold portions of the garment together. Such a button may be used to fixedly hold the portions together, so that a wearer cannot unbutton the portions, e.g. the button on the top of a hat. The button may be used to removably hold the portions together, so that a wearer can unbutton the portions, e.g. the button on the front of a dress shirt. The button may also connect two garments together, by being fixedly attached to a first garment, and allowing a second garment to be buttoned to the first garment. Similarly, the button may connect more than two garments together. To secure the portions, the button may connect with a connector located on the other portion, e.g. a snap button engages with a snap connector. As another way to secure portions, the button may slip through a hole located on the other portion. The button also may serve as ornamentation on the garment, e.g. the button is an accent to the look of the garment, and does not have a functional aspect. The button may have both a functional aspect and an ornamental aspect.

A button sensor may be used to monitor different biometrics of the body of the wearer of the garment. For example, a button sensor may be used to monitor temperature, oxygen content, blood component content, blood sugar content, heart rate, breathing rate, apnea, brain activity, altitude, cramps, bleeding, asthma attacks, anxiety attacks, loss of consciousness, high force impacts, a sudden fall, perspiration, moisture, velocity, movement, distance, location (with a GPS component), etc. To measure these different metrics, the button sensor may incorporate one or more sensors. For example, a thermostat to measure temperature, an accelerometer to measure motion, a audio sensor to detect noise, a light sensor to detect light (or wavelength(s) of light), an electromagnetic wave detector, a radio wave detector.

A button sensor has a transmitter to wirelessly send the data from the sensor to a remote receiver. A button sensor may act as a relay for a sensor that is located within a body. Thus, such a button may receive data from an internal sensor, and then broadcast the data to a receiver. The antenna for the transmitter may be located within the button, and/or be a part of the button (e.g., the holes or the shell). The antenna may also include passive elements that are exterior to the button. For example, the active elements may be located within the button, and the passive elements may comprise the wire that sews the button to the garment. In one embodiment, the antenna is woven into a garment with conductive thread and connected to the button sensor with conductive thread. Note that the button sensor may receive information as well. For example, the button may receive operational instructions, e.g., a command to take measurements, a command to send data, software updates, store data, analyze data, reset, deactivate, power down, and combinations thereof, etc.

The receiver includes a memory to record the data. The receiver may also include a processor and associated software to process the received data into information usable by a technician, nurse, doctor, or other medical practitioner. The receiver may be a handheld unit, such as a personal data unit, a cell phone, or other handheld computing unit. The receiver may also be a portable unit, such as a monitor. The portable unit may include physical connections for power and or data. The receiver may also comprise a fixed data collection point that is permanently mounted in the garment wearer's location. Such a receiver may be located in a hospital, retirement home, or other facility that provides medical care. In one embodiment, the receiver is in a vehicle, for example to operate with roadside assistance systems. In another embodiment, the receiver is coupled to public transportation, for example to operate with emergency warning systems. In yet another embodiment, the receiver is a cellular phone, operating with emergency 911 systems.

A sensing garment, or the garment having a button sensor, may comprise a single button sensor, or may comprise multiple button sensors. Each button sensor may sense a single metric or may sense multiple metrics. A sensing garment may have multiple button sensors, with some of the button sensors providing measurements of one metric and other buttons sensors providing measurements of one or more other metrics. Other sensing garments may have one or more buttons that measure a single metric and one or more buttons that measure multiple metrics.

The sensing garment may have multiple buttons sensing the same metric, with the data from the buttons being correlated to determine information of the metric. For example, one embodiment may have multiple button sensors to measure body temperature. The sensors may be located at different parts of the body. The receiver would then receive the data from the sensors, and knowing the position of the sensors, determine the temperature of the core of the body of the wearer.

The sensing garment may have multiple buttons sensing the same metric, with the data providing differential information to determine the metric. For example, an embodiment may have multiple button sensors to measure movement. The sensors may be located at different parts of the body, with one sensor located near the sternum, and another sensor located near the clavicle. As the wearer breathes, the sensor near the sternum would move, while the sensor near the clavicle would remain relatively stationary. The data from the sensor buttons could then be used by the receiver to determine a rate of breathing of the wearer.

In another embodiment, sensing garments on multiple living beings interact. In this embodiment, a sensor network collects social behavior data, such as social interactive patterns, and can facilitate detecting hostile, violent and/or dangerous events. In one example, the sensor network enables studying of interpersonal stimulus/response or unconscious interpersonal communication.

The button may use one or more technologies to transmit the information to the receiver. For example, the button may use a Bluetooth transmitter, an infrared transmitter, a wireless LAN-type transmitter, a short range cellular-type transmitter, a radio frequency (RF) transmitter, a GigaHertz range transmitter, etc.

The button sensor is fixedly attached to its associated garment. It may be attached by having thread or wire sewn through holes in the button sensor to the garment. It may also be attached by using a rivet that connects the button to the garment. In either event, the button sensor remains with the garment, and is hermetically sealed such that when the garment is washed and/or dried, the electronic aspects of the button sensor are not harmed. The button sensor is a material capable of withstanding water, exposure to corrosive materials such as laundry soap, bleach or other oxidizing agents, and the vibration and heat of a dryer. Suitable materials are known to exist, for example plastics or epoxies.

The button sensor is not coupled to an external power source, and thus the button sensor would have to store power sufficient for extended operations, to generate its own power, or both. Garments used in institutional settings, e.g. hospitals, may use sensor buttons that only have power storage. Such garments may be have the power supply recharged on a periodic basis. For example, many institutions change gowns on a daily basis (if not sooner). The power storage is able to power the button for a few days before a recharge is necessary. Furthermore, the operation of the buttons may be cascaded. For example, a gown may have two sensor buttons sensing the same metric, with only one button operating at a time. Thus, the second button would begin operations when the first button has exhausted its power supply. The first button may send a signal that is received by the second button to begin operations, or the receiver may send a signal to the second button to begin operations, after the receiver has stopped receiving data from the first button.

The button sensor may use one or more different types of power generation to provide itself power for its operations. For example, one type of power generation is solar power. The button sensor may include one or more solar panels that receive light and generate power from the light. The button sensor may also have an ambient RF or direct RF generator that uses radio frequency (RF) energy to generate power. Another type of power generation is piezoelectric power generation. The button sensor includes a piezoelectric device to generate power from vibration. For example, as the button sensor is bounced around in a washer and/or a dryer, the button generates power. Another type of power generation uses a thermocouple. The button sensor includes a thermocouple to generate power from a heat differential to which the button is exposed. The side of the button that is closer to the body is warmer than the side of the button facing away from the body. This temperature differential may be used to generate power. Another type of power generation uses a kinetic generator. The button sensor includes such a generator so that as the button is moved, it generates power. Other types of power generation include a chemical reaction.

In one embodiment, the power generator is attached to the garment (for example, a flexible solar panel on the back of a shirt) and coupled to the button sensor with conductive thread. In another embodiment, short range magnetic conduction, and/or wireless power is used for connectivity.

A sensing garment may have multiple buttons, with different ones of the buttons using different power generation methods. For example, one button may be using solar power to generate power, another button may be using a kinetic generation, and a further button may be using a thermocouple. Thus, at any given time, at least one of the buttons will be generating power.

Note that the location of the button on the garment may be used to select the type of power generation. For example, a long sleeve shirt may use kinetic generation for a button located on the sleeves, solar generation for a button located on the collar or upper chest, thermocouple for a button located on the lower chest, and infrared solar power for a button located at the bottom of the shirt (which may be tucked into pants).

Note that the metric to be sensed may select the type of power generation. For example, if the button is to measure movement, then the power button may use a kinematic generator. Thus, the button would generate power to measure the movement, and if there is no movement, there is no data needed to be taken, and thus no power is required or provided.

FIG. 1 depicts a perspective view of a button sensor 100, according to embodiments of the invention. In this arrangement, the button 100 would be secured to an article of clothing or garment via the holes 102. Thread, wire, pins, rivets, etc. would pass through the holes and connect the button to the garment. The button 100 includes a sealed container 101 that includes a wireless sensor (not shown) that would sense data for a metric from a living being wearing the garment. The wireless sensor is formed into a shape that allows the holes 102 to pass through the button 100 without interfering with the operation of the wireless sensor.

The button 100 can be formed using many different production processes. For example, the button 100 can be formed by using an injection molding process. The wireless sensor is placed into an injection mold. Material is then injected into the mold to encapsulate the wireless sensor and form the button 100. The holes 102 may then be drilled into the button or may be formed as part of the injection molding process. The button 100 can also be formed by using a package. The button is secured in a package. A lid is then welded, e.g. via ultrasonic welding, onto the package. The holes 102 already exist in the package and the lid. Either process results in a hermetically sealed button 100 that comprises the wireless sensor. Note that other processes may be used to form the button 100, as long as the button 100 is hermetically sealed and able to perform the functions described herein.

Figure 2A:
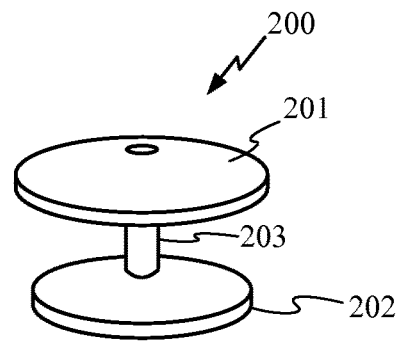
FIGS. 2A-2C respectively depict a perspective view, a side elevation view, and a bottom elevation view of another button sensor.
Figure 2B:
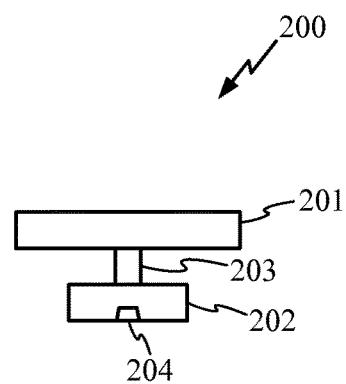
Figure 2C:
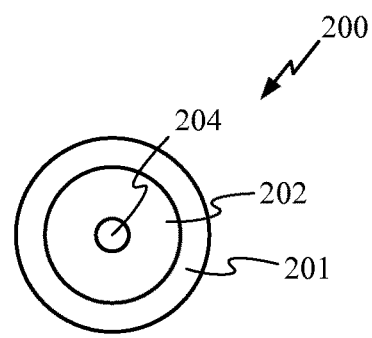

FIGS. 2A-2C respectively depict a perspective view, a side elevation view, and a bottom elevation view of another button sensor 200, according to embodiments of the invention. In this arrangement, the button 200 would be secured to an article of clothing or garment via an attachment assembly including a post 203 and a base 202. The button 200 has an upper portion 201 that is a sealed container and includes a wireless sensor (not shown) that would sense data for a metric from the living being wearing the garment. The button 200 is attached to a garment by passing the post 203 through the garment. The base 202 is then secured to the post by riveting the base 202 to the post 203. The base 202 may also be secured to the post 203 by an adhesive, welding (e.g. ultrasonic welding), screwing the base 202 to the post 203, friction, etc.

In this embodiment, the post 203 and the base 202 may perform functions beyond attaching the button 200 to the garment. The post 203 and the base 202 may comprise power storage and/or power generation aspects of the button 200. For example, the base 202 and/or the post 203 may include a battery, capacitor, or other power storage unit. Furthermore, the base 202 may serve as a heat sink for a thermocouple power generator. The base 202 is adjacent to or in contact with the body of the wearer of the garment, and thus is exposed to body heat. The upper portion is located away from the body, and is exposed to ambient temperature. The upper portion may then use the temperature differential to generate electricity. The post 203 would conduct the body heat from the base 202 to the upper portion 201. As another example, the base 202 may comprise an infrared solar panel to generate electricity from body heat.

The post 203 and the base 202 may also be part of the antenna of the button. For example, the base 202 may have a passive element energized by an active element located within the upper portion 201. The base 202 may also have an active element of the antenna that is connected to a signal source located within the upper portion 201 through the post 203.

The base 202 may also include a sensor 204 that is used to measure a metric of the wearer of the garment. The base 202 is adjacent to or in contact with the body of the wearer of the garment, and thus the sensor 204 would be able to more accurately measure the desired metric.

The button 200 may be formed by using either the injection molding process or the packaging process described above with respect to the button 100. Note that other processes may be used to form the button 200, as long as the button 200 is hermetically sealed and able to perform the functions described herein.

Figure 3:
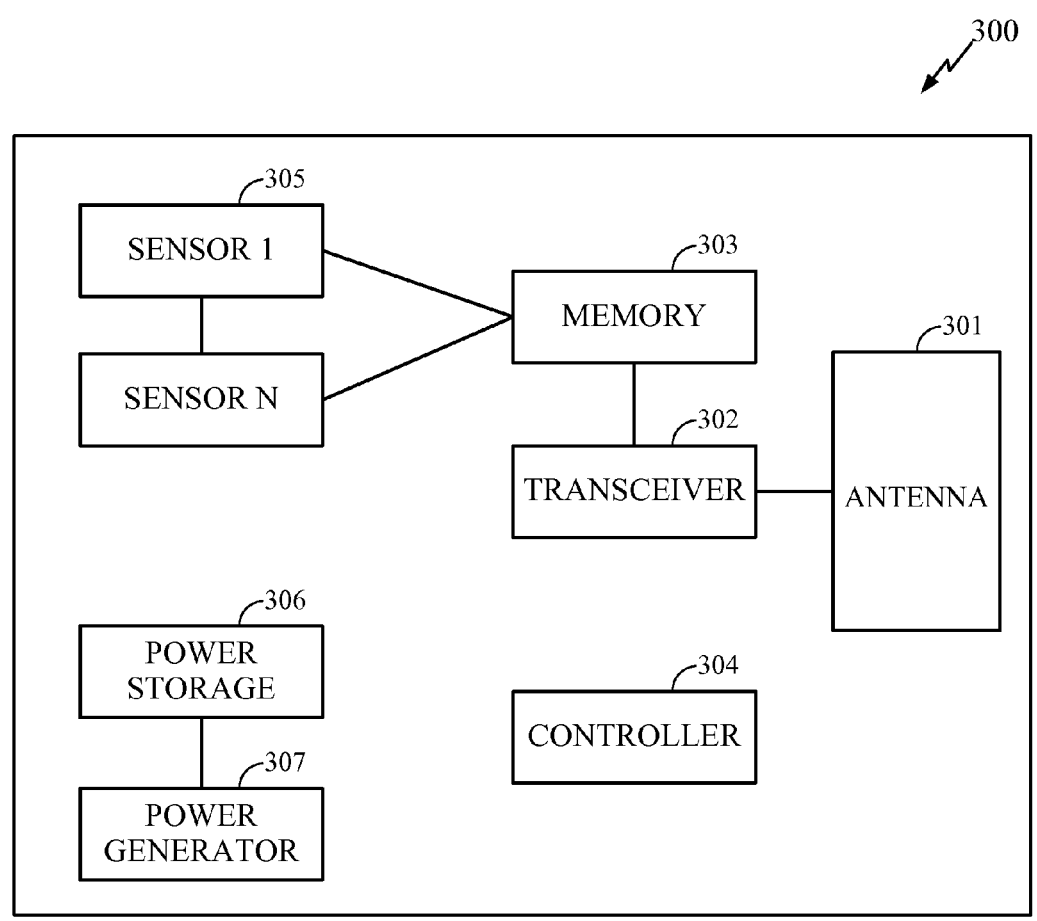
FIG. 3 depicts a block diagram showing an exemplary arrangement of a wireless sensor circuit that is embedded into the button sensor of FIG. 1 or FIG. 2A-2C.

FIG. 3 depicts a block diagram showing an exemplary arrangement of a wireless sensor circuit 300 embedded into a button sensor 100 or 200, according to embodiments of the invention. The circuit 300 uses a controller 304 to manage operations of the circuit 300. The controller 304 executes software that is stored in a memory 303 in performing its various functions. The circuit 300 includes at least one sensor 305 that measures a body metric. The circuit may include multiple sensors, each of which measures a different metric. The controller 304 may direct the sensor as to when and how long to take measurements. Alternatively, the sensor may be set to continuously take measurements. The data from the measurements is stored in the memory 303.

The circuit 300 uses a transceiver 302 to send the measured data to a receiver. The controller 304 may direct the transceiver 302 as to when to send data. Alternatively, the transceiver may be set to continuously send data. The transceiver 302 is coupled to an antenna 301 to send the data. The transceiver, via the antenna 301, may also receive data from an external source. The received data may be operating commands, e.g. turn on/off, send data, etc, or may be other information, e.g. software updates, etc.

The circuit 300 is self-powered and includes at least a power storage device 306 or power generator 307. The power storage device 306 may be a battery, a capacitor, or other power storage unit. In some situations, the power storage device may be able to be recharged on a periodic basis. For example, if the button is located on a garment that is used in an institutional setting, e.g. a hospital or retirement home, and the care of the garment is handled by the institution, then the power storage device may be recharged on a periodic basis. Alternatively, the circuit 300 includes a power generator 307 that generates power for use by the circuit 300. Excess power is stored in the power storage device 306. The controller 304 may direct the power generator 307 as to when to operate. Alternatively, the power generator 307 may be set to continuously operate, so long as capable. Note that the button may include a power generator or a power storage device, or both.

Figure 4A:
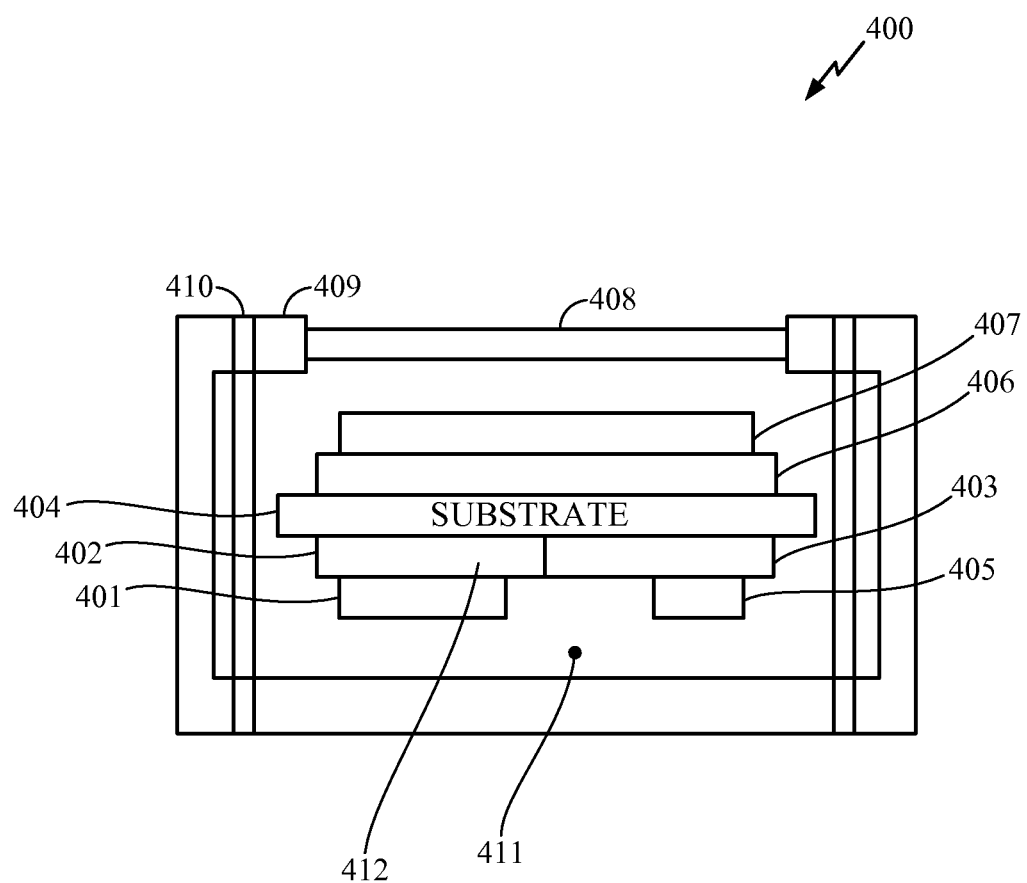
FIG. 4A depicts a cross-section of an exemplary circuit of the wireless circuit of FIG. 3 embedded in the button sensor of FIG. 1.

FIG. 4A depicts a cross-section of an exemplary structure 400 of the wireless circuit 300 of FIG. 3 embedded in the button sensor 100 of FIG. 1. The structure 400 in this arrangement is a through silicon stacked (TSS) integrated circuit. The various layers communicate with each other and be powered by vertical through silicon vias (TSVs). Note that this arrangement is by way of example only, as other types of circuits may be used.

The circuit 400 includes a package substrate 404, upon which other circuit components are stacked. The various components function as described in the preceding paragraphs. The circuit includes a controller 402, and a memory 403. The structure 400 also includes a power storage 406 and power generator 407. As an example, the structure 400 uses a solar panel as the power generator 407. Thus, a lid 409 includes a window 408 to allow light (either visible and/or infrared light) to reach the solar panel. The structure 400 also includes antenna 401 and transceiver 412. The sensor 405 of the circuit 400 is located on the side of the button that is adjacent to the body of the wearer. As an example, the sensor 405 receives the electromagnetic impulses that a heart generates in beating. Thus, the sensor 405 measures heart rate. In this example, the structure 400 is located in a package 410, and surrounded by material 411, such as a plastic or epoxy, to protect the circuit from damage. The connection between the lid 409 and the package 410 is hermetically sealed. The package may be formed by injection molding or insert molding.

Figure 4B:
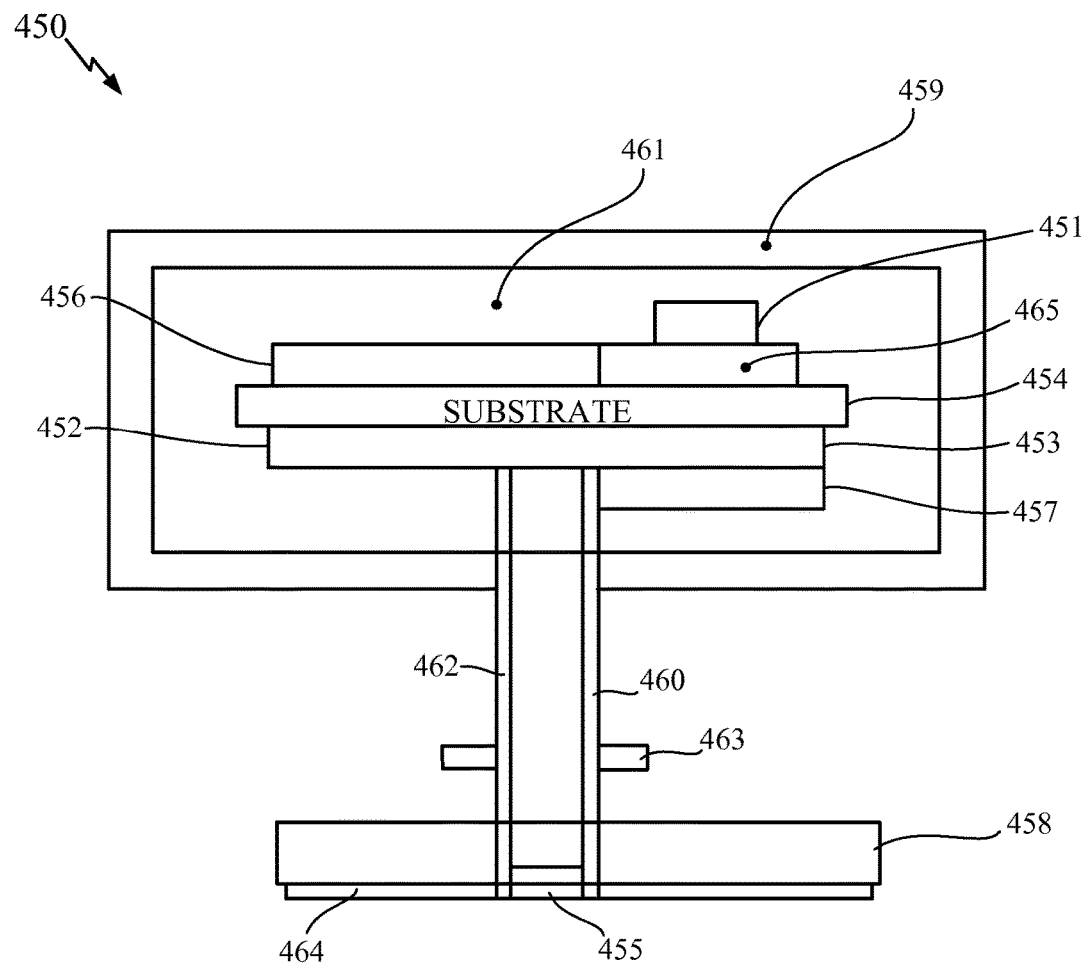
FIG. 4B depicts a cross-section of an exemplary circuit of the wireless circuit of FIG. 3 embedded in the button sensor of FIGS. 2A-2C.

FIG. 4B depicts a cross-section of an exemplary circuit 450 of the wireless circuit 300 of FIG. 3 embedded in the button sensor 200 of FIGS. 2A-2C. The circuit 450 in this arrangement is a through silicon stacked integrated circuit. The various layers would communicate with each other and be powered by vertical through silicon vias. Note that this arrangement is by way of example only, as other types of circuits may be used.

The circuit 450 includes a substrate 454, upon which other circuit components are stacked. The various components function as described in the preceding paragraphs. The circuit includes a controller 452, and a memory 453. The circuit 450 also includes a power storage 456 and a power generator 457. As an example, the circuit 450 uses a thermocouple as the power generator 457. Thus, heat from the body of the wearer is transmitted from the base 458 to the power generator 457. To facilitate heat transfer, the post 460 includes heat conductive material 462, e.g. a metal. Similarly, the base 458 also includes a heat conductive material 464. The metal may be coated with a material to prevent corrosion. The circuit 450 also includes an antenna 451 and a transceiver 465. The sensor 455 of the circuit 400 is located at the base of the post 460. This location places the sensor either directly in contact with the wearer or adjacent to the wearer. As an example, the sensor 455 detects the temperature of the wearer. In this example, the circuit is formed in a button that has been injection molded.

The button may include an outer layer 459 of a decorative material. The injection molding surrounds the circuit 450 with a material 461, such as plastic or epoxy. The package may be formed by injection molding or insert molding. A retaining clip 463 is also shown. The retaining clip 463 holds a garment between the retaining clip 463 and the base 458 to prevent the garment from riding up the post 460.

Figure 5:
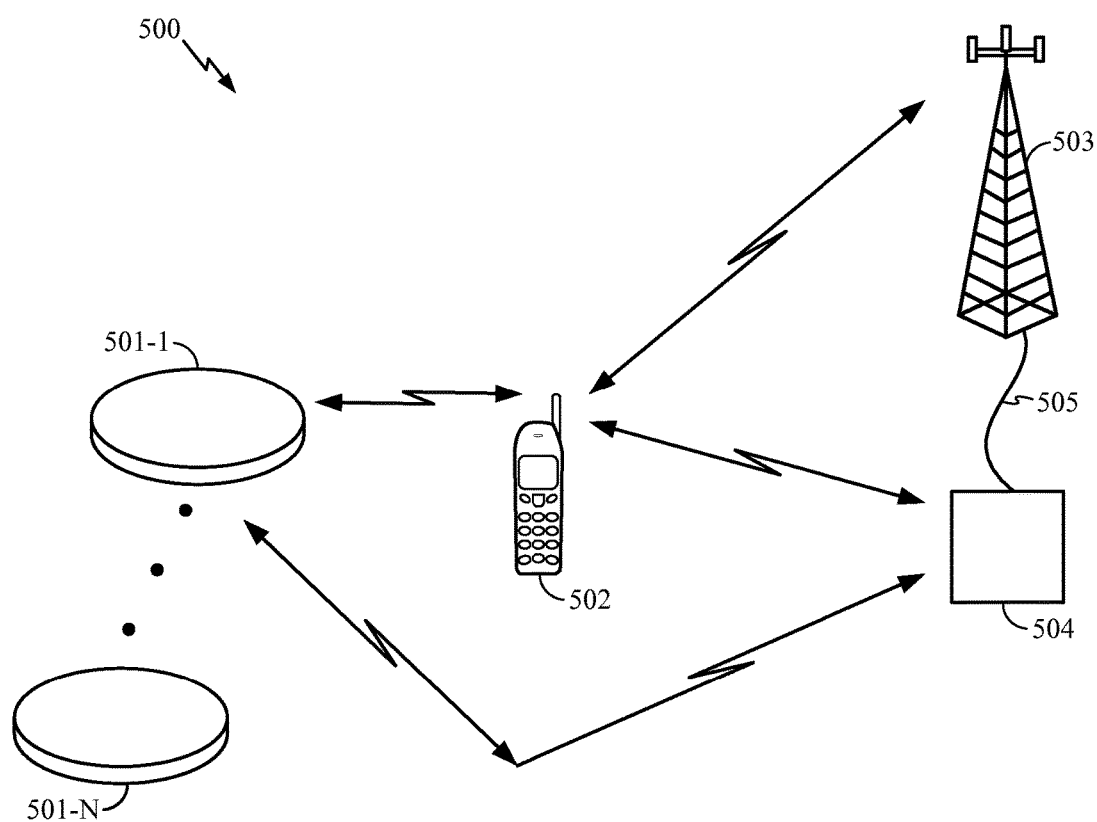
FIG. 5 is a schematic diagram of an exemplary arrangement of a wireless communication system that includes a button sensor of FIG. 1 or FIGS. 2A-2C.

FIG. 5 is a schematic diagram of an exemplary arrangement of a wireless communication system 500 that includes at least one button sensor 501-1, 501-*n*, of FIG. 1 and/or FIGS. 2A-2C. For purposes of illustration, FIG. 5 depicts multiple buttons 501-1 to 501-*n* communicating with receivers 502 and 504. The receiver 502 may be a hand-held receiver, such as cell phone or personal data assistant, while the receiver 504 may be fixed or portable, e.g. a base monitor, a meter reader, or laptop computer. Note that this is by way of example only, as there may only be one button, and there may be more/fewer receivers. The buttons 501-1-501-*n* may communicate with either receiver 502, 504. Each of the receivers may send data to or receive data from the buttons. The receivers 502, 504 may communicate with each, other either directly, or by using a cell system 503, or a cell system that is coupled to a land line system 505.

Although specific circuitry has been set forth, it will be appreciated by those skilled in the art that not all of the disclosed circuitry is required to practice the invention. For example, the controller and memory could be integrated into a single chip. Similarly, the power storage and power generator could be implemented as a single chip. Other combinations of separately shown (or combined) circuits are also contemplated. Moreover, certain well known circuits have not been described, to maintain focus on the invention.

Note that any of the functions described herein may be implemented in hardware, software, and/or firmware, and/or any combination thereof. When implemented in software, the elements of the present invention are essentially the code segments to perform the necessary tasks. The program or code segments can be stored in a processor readable medium. The "processor readable medium" may include any medium that can store or transfer information. Examples of the processor readable medium include an electronic circuit, a semiconductor memory device, a ROM, a flash memory, an erasable ROM (EROM), a floppy diskette, a compact disk CD-ROM, an optical disk, a hard disk, a fiber optic medium, etc. The code segments may be downloaded via computer networks such as the Internet, Intranet, etc.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A button adapted for use on a garment, comprising:
a sensor configured to sense multiple metrics operable to provide data of at least one metric to monitor health of a wearer of the garment;
a transceiver coupled to the sensor and being operable to transmit the data and to receive commands;
a power source having multiple sources of power generation coupled to the sensor and being operable to provide power to the transceiver, wherein a source of power generation for at least one of the sensor and transceiver is selectable from the multiple sources of power generation based on a location of the sensor on the wearer of the garment;
a power storage device coupled directly to the power source;
a controller configured to direct the transceiver as to when to transmit the data; and
a hermetically sealed housing including the sensor, the transceiver, the controller, the power source, and the power storage device within the hermetically sealed housing, the hermetically sealed housing being configured to be secured to a portion of the garment.

2. The button of claim 1, wherein the button is adapted to relay the data received by an external receiver to the transceiver.

3. The button of claim 1, wherein a hole is defined through the button to allow the button to be secured to the portion of the garment.

4. The button of claim 1, further comprising:
a post having a proximal end and a distal end, the proximal end coupled to a portion of the button; and
a base adapted to be coupled to the distal end of the post, wherein the base is spaced apart from the button and the post and the base are adapted to secure the button to the portion of the garment.

5. The button of claim 4, wherein at least a portion of the power source is disposed in the base.

6. The button of claim 4, wherein at least a portion of the sensor is disposed in the base and the sensor comprises multiple sensors.

7. The button of claim 1, further comprising a memory operable to store the data of one or more metrics related to the wearer of the garment and coupled to the sensor and to the transmitter.

8. The button of claim 1, further comprising an antenna coupled to the transmitter.

9. The button of claim 1, wherein the metric comprises temperature, oxygen content, blood component content, blood sugar content, heart rate, breathing rate, apnea, brain activity, velocity, movement, distance, and/or location.

10. The button of claim 1, wherein the housing is further configured to secure the portion of the garment to a second portion of the garment.

11. The button of claim 1, wherein the garment is at least one of the following:
shirt, pair of pants, hat, mask, underwear, brassiere, hospital gown, vest, belt, jewelry, hand bag, wallet, jacket, sweat band, socks, shoes, boots.

12. The button of claim 1, further comprising a controller configured to direct the power source having multiple sources of power generation.

13. The button of claim 12, wherein the at least one metric to be sensed selects the source of power generation for the button.

14. A button adapted for use on a garment, comprising:
a sensor configured to sense multiple metrics operable to provide data of at least one metric to monitor health of a wearer of the garment, wherein the sensor is comprised of multiple sensors, each sensing a different metric as directed by a controller and further wherein a metric to be sensed determines a source of power generation;
a transceiver coupled to the sensor and being operable to transmit the data and to receive commands;
the source of power generation having multiple sources of power generation coupled to the sensor and being operable to provide power to the transceiver;
a power storage device coupled directly to the power source;
the controller configured to direct the transceiver as to when to transmit the data; and
a hermetically sealed housing including the sensor, the transceiver, the controller, the power source, and the power storage device within the hermetically sealed housing, the hermetically sealed housing being configured to be secured to a portion of the garment.

15. A method of manufacturing a button, comprising:
selecting a housing;
locating, inside the housing, a sensor configured to sense multiple metrics operable to measure data of at least one metric related to monitor health of a wearer of a garment;
locating, inside the housing, a transceiver coupled to the sensor and being operable to transmit the data to an external receiver and to receive commands;
locating, inside the housing, a controller configured to direct the transceiver as to when to transmit the data;
locating, inside the housing, a power source having multiple power generation sources being operable to provide power to the controller and transceiver, or to the controller, transceiver, and sensor, wherein a source of power generation for at least one of the sensor and transceiver is selectable from the multiple sources of power generation based on a location of the sensor on the wearer of the garment;
locating, inside the housing, a power storage device connected directly to the power source; and
hermetically sealing the sensor, the transceiver, the controller, and the power source inside the housing, wherein the housing is configured to be secured to a portion of the garment as the button.

16. The method of claim 15, wherein the button is hermetically sealed by injection molding.

17. The method of claim 15, wherein the power source is selected based on a location of the button on the garment.

18. The method of claim 15, wherein the power source is a type that generates power from solar power, thermocouple power, kinetic power, ambient radio frequency (RF) power, directed RF power, piezoelectric power, and/or chemical power.

19. A method of manufacturing a button, comprising:
selecting a housing;
locating, inside the housing, a sensor configured to sense multiple metrics operable to measure data of at least one metric related to monitor health of a wearer of a garment;
locating, inside the housing, a transceiver coupled to the sensor and being operable to transmit the data to an external receiver and to receive commands;
locating, inside the housing, a controller configured to direct the transceiver as to when to transmit the data;
locating, inside the housing, a power source having multiple power generation sources being operable to provide power to the controller and transceiver, or to the controller, transceiver, and sensor, wherein the power source having multiple power generation sources is configured to select a power generation source based on a type of metric to be measured by the sensor;
locating, inside the housing, a power storage device connected directly to the power source; and
hermetically sealing the sensor, the transceiver, the controller, and the power source inside the housing, wherein the housing is configured to be secured to a portion of the garment as the button.

20. A button adapted for use on a garment, comprising:
means for sensing data of a metric related to health of a wearer of the garment, wherein the means for sensing is configured to sense multiple metrics;
means for transceiving the data coupled to the sensing means;
means for providing power from multiple power generation sources to the transceiving means coupled to the sensing means, wherein the means for providing power from multiple power generation sources is configured to select a source of power generation based on a location of the sensor on the wearer of the garment;
means for storing power, wherein the means for storing power is directly connected to the means for providing power; and
means for hermetically housing the sensing means, the transceiving means, and the power providing means, and the power storing means within a housing means, the housing means being configured to be secured to a portion of the garment.

* * * * *